(12) United States Patent
Yamada

(10) Patent No.: US 9,074,962 B2
(45) Date of Patent: Jul. 7, 2015

(54) LIQUID LEAKAGE DETECTOR, LIQUID TRANSPORT APPARATUS AND METHOD OF DETECTING LIQUID LEAKAGE

(75) Inventor: Kazuhiro Yamada, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 813 days.

(21) Appl. No.: 13/207,704

(22) Filed: Aug. 11, 2011

(65) Prior Publication Data

US 2012/0038912 A1      Feb. 16, 2012

(30) Foreign Application Priority Data

Aug. 16, 2010   (JP) ................................ 2010-181768

(51) Int. Cl.
| | |
|---|---|
| *G01N 21/00* | (2006.01) |
| *D06F 39/08* | (2006.01) |
| *F16J 3/00* | (2006.01) |
| *G01M 3/18* | (2006.01) |
| *G01M 3/16* | (2006.01) |
| *G01M 3/38* | (2006.01) |
| *G01N 21/49* | (2006.01) |

(52) U.S. Cl.
CPC . *G01M 3/18* (2013.01); *G01M 3/16* (2013.01); *G01M 3/38* (2013.01); *G01N 21/49* (2013.01)

(58) Field of Classification Search
CPC .............. B41J 29/13; B41J 2/20; G01M 3/38; G01M 3/047; G01M 11/31; G01M 3/40; G01M 3/16
USPC ...................................... 356/240.1, 73.1, 442
See application file for complete search history.

(56) References Cited

U.S. PATENT DOCUMENTS

| | | | |
|---|---|---|---|
| 5,796,097 A | * | 8/1998 | Lawrence ...................... 250/229 |
| 6,402,277 B1 | | 6/2002 | Monclus et al. |
| 6,484,564 B1 | * | 11/2002 | Hayashida ......................... 73/40 |
| 2009/0066339 A1 | * | 3/2009 | Glezer et al. ................... 324/444 |
| 2011/0157283 A1 | * | 6/2011 | Sugahara ......................... 347/86 |

FOREIGN PATENT DOCUMENTS

| | | |
|---|---|---|
| JP | 63-266340 A | 11/1988 |
| JP | H05-014216 B | 2/1993 |
| JP | 06-340089 A | 12/1994 |
| JP | 3162547 B2 | 5/2001 |
| JP | 3288921 B2 | 6/2002 |
| JP | 2006-231803 A | 9/2006 |

* cited by examiner

*Primary Examiner* — Tarifur Chowdhury
*Assistant Examiner* — Sunghee Y Gray
(74) *Attorney, Agent, or Firm* — Canon USA Inc IP Division

(57) ABSTRACT

A liquid leakage detector includes: a first liquid detection unit provided at a member to be detected, the first liquid detection unit being configured to detect a liquid leaked from the member to be detected; a liquid impermeable member which covers the first liquid detection unit to protect the same from the ambient air; and a determining unit configured to determine whether the liquid is leaking from the member to be detected in response to a signal from the first liquid detection unit.

10 Claims, 12 Drawing Sheets

LIQUID LEAKAGE DETECTOR, LIQUID TRANSPORT APPARATUS AND METHOD OF DETECTING LIQUID LEAKAGE

BACKGROUND OF THE INVENTION

1. Field of the Invention

The present invention relates to a liquid leakage detector for detecting leakage of a liquid, such as contaminated liquids, a liquid transport apparatus which incorporates the liquid leakage detector, and a method of detecting liquid leakage.

2. Description of the Related Art

From the viewpoint of safety or environmental conservation, there is an increasing demand for techniques to detect leakage of liquids, such as organic solvents and contaminated liquids of chemicals. A configuration using plastic clad fiber (PCF) has been proposed as one of the leakage detection techniques. The PCF-based technique employs an optical fiber constituted by a core and a cladding which wraps the core. The cladding is made of a light absorbing material. Leakage is detected based on an increase in light propagation loss in the optical fiber due to a change in the refractive index of the cladding to which the liquid adheres or through which the liquid permeates. In addition to the detection of liquid leakage, a site of leakage is detected in this technique by determining a distribution of propagation loss in the direction of a light beam path in the using, for example, an optical time-domain reflectmeter (OTDR) device.

Japanese Patent Laid-Open No. 63-266340 proposes a technique of detecting liquid leakage based on an increase in propagation loss when an optical fiber is bent using a material which swells when a liquid permeates the same.

Recently, inkjet printers, which were typically intended for home use, have been applied to a wide variety of fields; in the business field, inkjet printers are used in offices or for retail photographing and, in the industrial field, inkjet printers are used for drawing electronic circuits and manufacturing flat panel displays. Inkjet printers for business use should have high speed printing performance. In such high speed printing, however, in the event that ink leakage occurs in an ink supply unit, the leakage should be detected promptly and the recording operation should be stopped immediately; otherwise, defective printed matters will increase in number in a short time and, as a result, users will suffer serious loss in their commercial products.

Since printers for business use should be equipped with a large-sized ink tank for mass printing, an "off-carriage" system is often employed in which recording heads are separated from the ink tank and ink is supplied through an ink tube. In some printers employing this system, the recording heads are connected to the ink tank via the ink tube and the ink tank is pressurized to supply the ink to the recording heads. In such printers, even a very small amount of ink leakage may easily scatter inside the printer, which leads to a possibility of contamination inside the printer and an increased range of corrosion damage of the printer. For this reason, it is required to detect ink leakage promptly and correctly. In the printers for business use, unlike printers for consumer use, there is a demand for shorter standby time and longer print operation time in order for improved equipment operation efficiency. For this reason, a technique of constant detection of ink leakage without any interruption of ink supply is required in the printers for business use.

The following methods, for example, have been proposed for constant detection of ink leakage during the supply of ink:

1. detecting leakage of ink at an electrode for leakage detection using electrical conductivity of ink (U.S. Pat. No. 6,402,277 and Japanese Patent No. 3162547);
2. detecting leakage of ink by detecting changes in reflectivity or an amount of transmitted light in an ink detection unit (Japanese Patent No. 3288921); and
3. detecting leakage of ink using an ink detection member which changes in shape when brought into contact with ink (Japanese Patent Laid-Open No. 06-340089 and Japanese Patent Laid-Open No. 2006-231803).

In the configuration of the PCF-based liquid leakage detector and the configuration proposed in Japanese Patent Laid-Open No. 63-266340 described above, however, have a deficiency that false detection of leakage will be made when the configuration is applied to monitoring leakage in the pipe of liquids, such as contaminated waste water. That is, these configurations may detect adhesion of liquid droplets to the PCF or a swelling material caused by high humidity or dew condensation in a surrounding environment of the pipe for the liquid as liquid leakage when no leakage occurs actually.

In inkjet printers, ink droplets are normally floating as fine mist which adheres to and deposit on surfaces of various members constituting the printers. For this reason, there is a possibility that the configurations proposed in the Patent Documents mentioned above make false detection of ink leakage when the ink mist adheres to and deposit on the liquid detection unit.

SUMMARY OF THE INVENTION

The present invention provides a liquid leakage detector, a liquid transport apparatus and a method of detecting liquid leakage capable of overcoming the above-described problems, preventing false detection of liquid leakage and correctly detecting liquid leakage.

In order to achieve the above object, the liquid leakage detector includes: a first liquid detection unit provided at a member to be detected, the first liquid detection unit being configured to detect a liquid leaked from the member to be detected; a liquid impermeable member which covers the first liquid detection unit to protect the same from the ambient air; and a determining unit configured to determine whether the liquid is leaking from the member to be detected in response to a signal from the first liquid detection unit.

Further features of the present invention will become apparent from the following description of exemplary embodiments with reference to the attached drawings.

DESCRIPTION OF THE EMBODIMENTS

Hereinafter, embodiments of the present invention will be described with reference to the drawings. The scope of the present invention, however, is at least defined by the claims and, therefore, the following description is in no way restrictive. For example, the shapes and arrangements illustrated in the following description do not restrict the scope of the present invention.

First, a liquid leakage detector according to a first embodiment will be described in detail.

The liquid leakage detector according to the first embodiment includes a liquid detection unit as a first liquid detection unit. The liquid detection unit may be fixed to a site with a possibility of liquid leakage in the pipe for the liquid as a member to be detected and detects a liquid leaked from that site. The liquid leakage detector also includes a liquid impermeable member and a control unit. The liquid impermeable member covers the site with a possibility of liquid leakage and the liquid detection unit to protect the same from the ambient air. The control unit may function as a determination unit which determines whether liquid leakage occurs in the site with a possibility of liquid leakage in response to a signal from the liquid detection unit.

Figure 1:
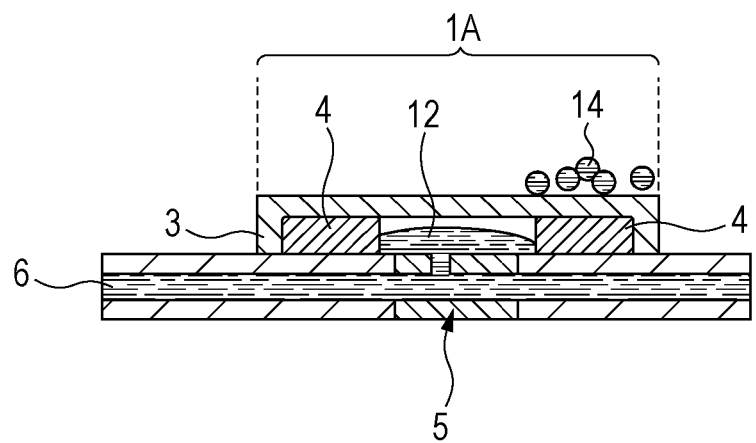
FIG. 1 is a schematic diagram illustrating a configuration of a liquid leakage detector according to a first embodiment incorporating an electrical unit as a liquid detection unit, and a state in which leakage occurs.

Exemplary Configuration of Liquid Leakage Detector Incorporating Electrical Unit FIG. 1 illustrates an example of a liquid leakage detector according to a first embodiment, which is an exemplary configuration incorporating an electrical unit as a liquid detection unit. In this exemplary configuration, an electrically conductive liquid is detected. As illustrated in FIG. 1, the liquid leakage detector includes a liquid detection unit 1A and a liquid impermeable member 3. The liquid detection unit 1A includes a pair of electrodes 4 fixed to an area near the site with a possibility of liquid leakage 5 in the pipe for the liquid. The liquid impermeable member 3 covers the site with a possibility of liquid leakage 5 and the liquid detection unit 1A to protect the same from the ambient air.

The pair of electrodes 4 is arranged on both sides of a gap which constitutes a site with a possibility of leakage of droplets. The electrodes 4 are electrically connected to a control unit (not illustrated) and are electrically conductive. The electrodes 4 can be made of, for example, a corrosion resistance material, such as noble metals and carbon. If the electrodes are made of a material which forms an insulating coat, such as an oxide, on its surface by corrosion, electrical conduction between the electrodes is inhibited when leakage occurs and, as a result, the leakage cannot be detected. The voltage applied between the electrodes 4 may be selected not to cause electrolysis of the liquid and the electrodes themselves upon leakage detection from the viewpoint of safety.

The liquid impermeable member 3 may be disposed on the liquid detection unit 1A to cover the entire surface which is in contact with the ambient air other than a surface on which the liquid detection unit 1A is fixed to the site with a possibility of liquid leakage 5. Here, the surface on which the liquid detection unit 1A is fixed to the site with a possibility of liquid leakage 5 is a surface on which a member constituting the site with a possibility of liquid leakage 5 is in contact with the liquid detection unit 1A. The liquid impermeable member 3 has a function to separate the liquid to be detected from the gap defined between the pair of electrodes 4, and can be made of a material which causes no chemical reaction with the liquid.

The site with a possibility of liquid leakage 5 is a position with an especially increased possibility of occurrence of the leakage in the liquid path. Specifically, the site with a possibility of liquid leakage 5 may be, for example, a connecting portion in the liquid path, a splicing portion of the member of the liquid path, a portion subject to repeated deformation, a portion subject to repeated vibration or temperature change and a portion exposed to an environment in which the member of the liquid path corrodes. Note that the liquid path may include a plurality of sites with a possibility of liquid leakage 5 or the entire area of the liquid path may be the site with a possibility of liquid leakage 5. Monitoring the entire area of the liquid path may require multiple liquid detection units or a large-sized liquid detection unit; thus, monitoring only sites especially with a possibility of leakage is desired from the viewpoint of cost.

Operation for Leakage Detection

With reference to FIG. 1, a state in which leakage occurs and an operation for detection of the leakage in an inkjet printer incorporating the liquid leakage detector with the configuration described above will be described in detail. Note that, in the present embodiment, the liquid "ink" is not limited to color ink for printing; the ink also includes various application materials, such as colorless ink for, for example, fixation use, ink containing metallic fine particles for drawing electronic circuits and a liquid used in manufacturing a flat panel display (FPD). Examples of the liquid used in manufacturing an FPD include a color filter material for the liquid crystal display and an organic electroluminescence light emitting material.

If a liquid (i.e., ink) leaks from the site with a possibility of liquid leakage 5 as illustrated in FIG. 1, a leaked liquid 12, i.e., the leaking ink, spreads between the pair of electrodes 4 and forms an electrical conductive path and, as a result, electrical resistance between the pair of electrodes 4 may be lowered. In response to the detection of the lowered electrical resistance between the pair of electrodes 4, the control unit determines that ink leakage has occurred.

In some inkjet printers, ink mist usually scatters inside the inkjet printers and adheres to and deposit on areas near the site with a possibility of liquid leakage 5. Adhesive droplets 14 illustrated in FIG. 1 represent the ink mist. In a case in which the ink does not leak but the ink mist adheres to and deposits on areas near the site with a possibility of liquid leakage 5, entering of ink between the pair of electrodes 4 is prevented by the liquid impermeable member 3 which covers the electrodes 4; there is therefore no change in electrical resistance between the electrodes 4 in the liquid detection unit 1A. Thus, no false detection of ink leakage is made. In the liquid leakage detector illustrated in FIG. 1, no false detection caused by the ink mist is made and thus the ink leakage can be detected correctly.

Figure 5:
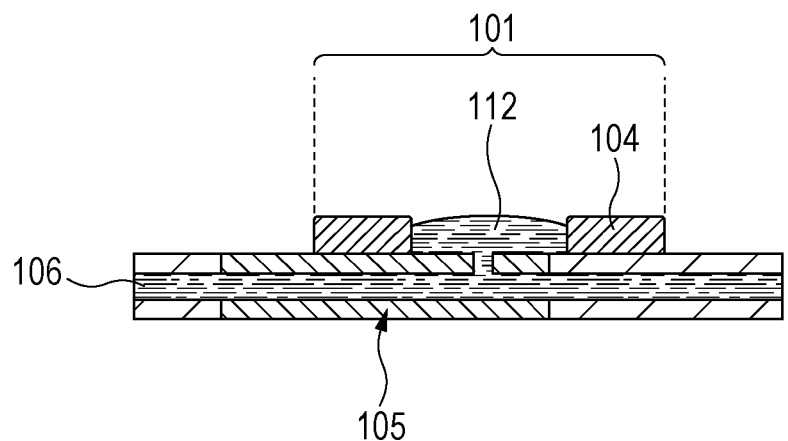
FIG. 5 is schematic diagram illustrating a configuration of a related art liquid leakage detector incorporating an electrical unit as a liquid detection unit, and a state in which leakage occurs.
Figure 6:
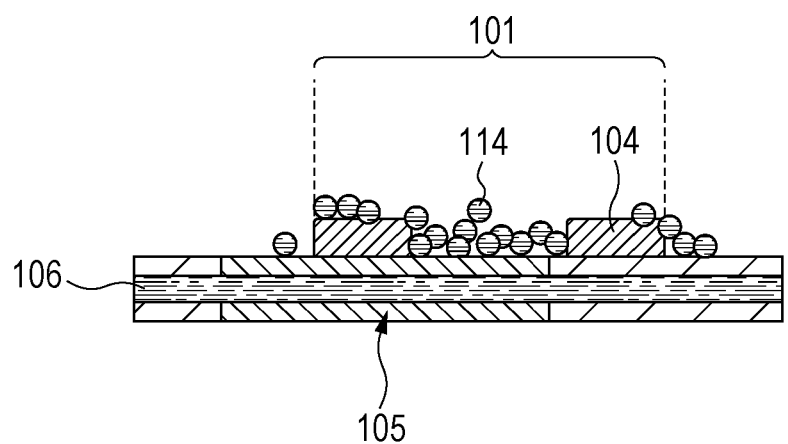
FIG. 6 is a schematic diagram illustrating a configuration of a related art liquid leakage detector incorporating an electrical unit as a liquid detection unit, and a state in which droplet adhesion occurs.

For comparison, a configuration of a related art liquid leakage detector incorporating an electrical detection unit for inkjet printers is illustrated in FIG. 5. In the configuration illustrated in FIG. 5, when a liquid 106 leaks as the leaked liquid 12, leakage can be detected based on a change in electrical resistance in response to the contact of leaking ink between a pair of electrodes 104. In the related art liquid leakage detector, however, includes no liquid impermeable member 103 which covers a liquid detection unit 101 to protect the same from the ambient air. For this reason, even in a state in which no liquid leakage occurs as illustrated in FIG. 6, if ink mist adheres to and deposit on the pair of electrodes 104 and an electrical conductive path is formed between the pair of electrodes 104, false detection of ink leakage will be made.

Figure 2:
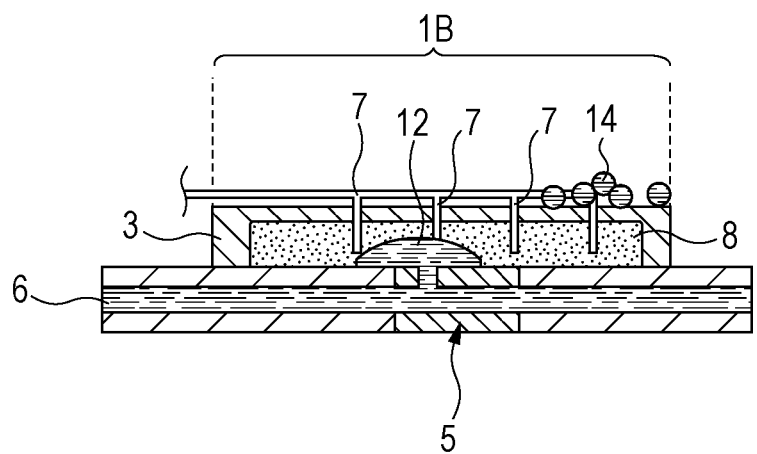
FIG. 2 is a schematic diagram illustrating a configuration of the liquid leakage detector according to the first embodiment incorporating an optical unit as a liquid detection unit, and a state in which leakage occurs.

First Exemplary Configuration of Liquid Leakage Detector Incorporating Optical Unit FIG. 2 is an example of the liquid leakage detector according to the first embodiment and is an exemplary configuration incorporating an optical unit as a liquid detection unit. With this configuration, unlike the configuration illustrated in FIG. 1, it is possible to detect a non-electrically conductive liquid, an oil-based liquid, such as solvent ink and an inflammable liquid in addition to the electrically conductive liquid.

In the configuration illustrated in FIG. 2, a liquid detection unit 1B is fixed to an area near the site with a possibility of liquid leakage 5 of the pipe for the liquid and is covered with the liquid impermeable member 3. The liquid detection unit 1B includes an absorber 8 and an optical fiber pair 7 of which ends are embedded in the absorber 8.

The absorber 8 may be made of, for example, a porous material, gel and resin of materials which does not chemically react with the liquid. The absorber 8 may be an absorber consisting of a substance which has a wavelength band to be absorbed or transmitted, which wavelength band is different from that of the liquid to be detected. Alternatively, an absorber in which fine particles of such a substance are dispersed may also be used.

Figure 3:
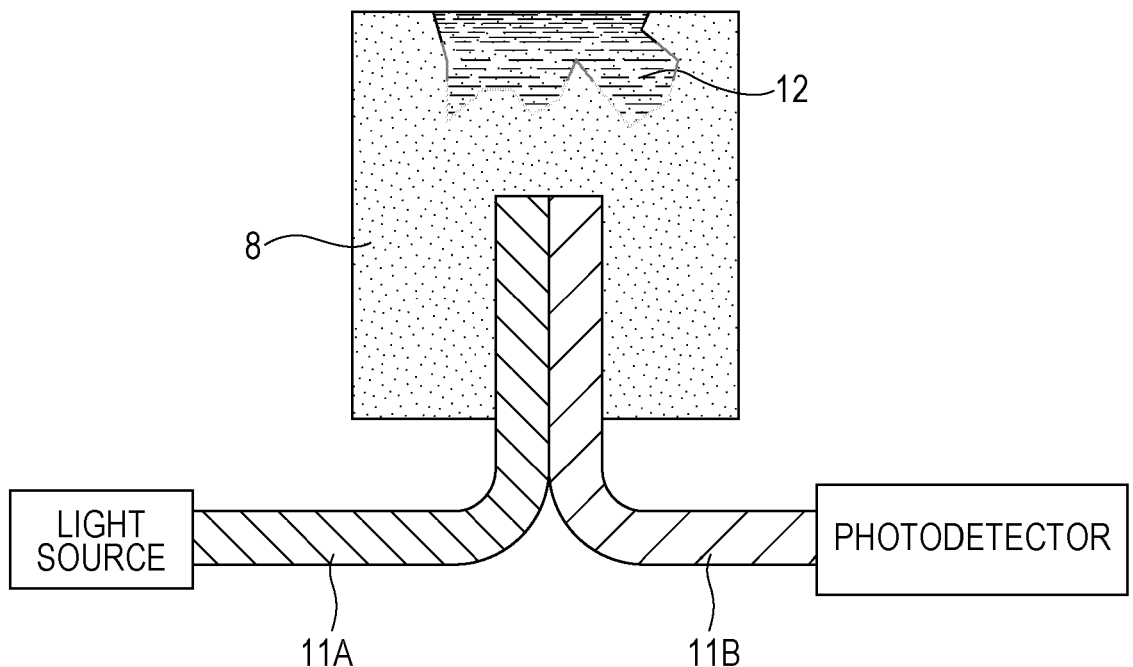
FIG. 3 is a schematic diagram illustrating an arrangement of an optical fiber pair and an absorber of the configuration illustrated in FIG. 2.

The optical fiber pair 7 is constituted by a light guiding optical fiber 11A and a light receiving optical fiber 11B. One of the ends (i.e., a detecting point) of each of these fibers 11A and 11B is embedded in the absorber 8 as illustrated in FIG. 3. The liquid detection unit 1B includes a light emitting unit and a light receiving unit as measuring units which measure changes in the optical property occurring in the absorber 8.

The other end of the light guiding optical fiber 11A is optically connected to a light source which constitutes the light emitting unit, and the other end of the light receiving optical fiber 11B is optically connected to a photodetector which constitutes the light receiving unit.

Light irradiated by the light emitting unit is emitted from the one end of the light guiding optical fiber 11A and light entering from the one end of the light receiving optical fiber 11B is received by the light receiving unit. During this process, changes in the optical property in the absorber 8 are measured and thus the liquid leaked in the site with a possibility of liquid leakage 5 is detected.

The configuration of the light source which constitutes the light emitting unit is not particularly limited as long as it can generate light that has at least a wavelength absorbed in or reflected by the liquid of which leakage is to be detected. The configuration of the photodetector which constitutes the light receiving unit is not particularly limited as long as it at least functions to detect light of the wavelength generated by the light source.

In the absorber 8, the optical fiber pair 7 emits light from the end of the light guiding optical fiber 11A and simultaneously receives the scattered light from the end of the light receiving optical fiber 11B. If leakage occurs at the site with a possibility of liquid leakage 5 near the optical fiber pair 7, the liquid is absorbed in the absorber 8 and therefore the amount of scattered light at an area near the optical fiber pair 7 in the absorber 8 changes. For example, the amount of scattered light of a wavelength band which the liquid absorbs is reduced. As a result, the existence of the liquid can be detected based on the change in the amount of scattered light received by the light receiving unit.

Further, correspondence data of the amount of liquid per unit volume absorbed in the absorber and the amount of reduction in scattered light may be prepared in advance; thus it is possible to detect the amount of liquid per unit volume at a leakage detection point based on the amount of scattered light received by the light receiving unit in accordance with the correspondence data.

Only one optical fiber pair 7 may be provided in the absorber 8 as described above; however, two or more, i.e., a plurality of optical fiber pairs 7 may be provided in the absorber 8 as illustrated in FIG. 2 to increase a leakage detection range. If a plurality of optical fiber pairs 7 are provided, a site of the leakage, a spreading range of the leakage and a spreading speed can be detected in addition to the existence of the leakage in response to signals from each of the optical fiber pairs 7 and temporal changes in the signals. The amount of the leaked liquid and a leakage rate (i.e., the amount of leaked liquid per unit time) in the absorber 8 can be estimated with the data of the amount of liquid per unit volume, the spreading range of the leakage and the spreading speed at areas near each of the optical fiber pairs.

Although the optical fiber pairs in FIG. 2 are illustrated to branch from a single optical fiber, the optical fiber pairs are bundled together and each pair is optically connected to the photodetector independently.

Description of Operation for Leakage Detection

An operation for leakage detection in the inkjet printer incorporating the liquid leakage detector of the configuration illustrated in FIG. 2 will be described in detail.

If leakage occurs at the site with a possibility of liquid leakage 5, the amount of scattered light in the absorber 8 at areas near the optical fiber pair 7 changes because the leaked ink is absorbed in the absorber 8. At this time, for example, the amount of scattered light of the wavelength band which ink absorbs is reduced. If a reduction in the amount of scattered light in the liquid detection unit 1B is detected, the control unit determines that leakage has occurred. The plurality of optical fiber pairs 7 not only can detect the existence of the leakage but can detect a site of the leakage and a leakage rate.

In a case in which no leakage has occurred but adhesive droplets (in this case, ink mist) 14 adhere to and deposit on the site with a possibility of liquid leakage 5, the liquid impermeable member 3 inhibits the ink mist to enter the absorber 8 and thus no change occurs in the amount of scattered light; thus the liquid detection unit 1B does not make false detection of ink leakage. In this manner, in the liquid leakage detector illustrated in FIG. 2, false detection due to adhesion of the ink mist is prevented and the ink leakage can be detected correctly.

As compared with a related art optical liquid detection unit incorporating an OTDR device, the liquid detection unit according to the embodiment illustrated in FIG. 2 has several more advantageous effects.

A related art liquid leakage detector incorporating the PCF includes a single optical fiber and is thus easy to install. Once leakage is detected in the related art liquid leakage detector, it may be necessary to replace the entire optical fiber because only a part of a cladding of the optical fiber at which the liquid is absorbed cannot be separated for replacement. Also, in the liquid leakage detector proposed in Japanese Patent Laid-Open No. 63-266340 mentioned above, since bending deflection remains in the optical fiber after the leakage detection, it is necessary to replace each optical fiber after the leakage detection.

In the liquid detection unit according to the embodiment of the configuration illustrated in FIG. 3, however, it is easy to replace the absorber after the leakage detection and components other than the absorber can be reused; thus monitoring of the leakage can be achieved with reduced cost.

In the PCF and the liquid detection unit proposed in Japanese Patent Laid-Open No. 63-266340, the OTDR device detects the liquid at a site with a possibility of liquid leakage with the position resolution of about 1 to 10 cm. If, therefore, the dimension of the site with a possibility of liquid leakage (e.g., a connecting portion) is smaller than that detectable with the position resolution, it is difficult to locate the site of leakage though the occurrence of leakage can be detected.

The liquid detection unit according to the embodiment illustrated in FIG. 3, however, includes a plurality of optical fiber pairs 7 arranged at intervals of 1 cm or shorter. It is therefore possible to detect occurrence of leakage and to locate the site of leakage even if the dimension of the site with a possibility of liquid leakage is small. The intervals between the optical fiber pairs 7 may be longer than a scattering distance of the scattered light to prevent mutual interference of the scattered light. The position resolution in the liquid detection unit can be increased by, for example, controlling the optical property of the absorber or providing a partition of a non-light transmissive member in the absorber to shorten the intervals between the optical fiber pairs 7.

In the liquid detection unit according to the embodiment illustrated in FIG. 3, leakage can be monitored without any false detection in flexible pipes, which are bent flexibly during the liquid supply operation, including an ink tube and a movable connector which connect the recording heads with the ink tank. In the related art, liquid detection unit in which propagation loss in the optical fiber is measured by the OTDR method, however, if a PCF is installed in the flexible pipe, an increase in propagation loss due to bending of the flexible pipe is added to the increase in propagation loss due to leakage. This results in lowered sensitivity and false detection.

Figure 4:
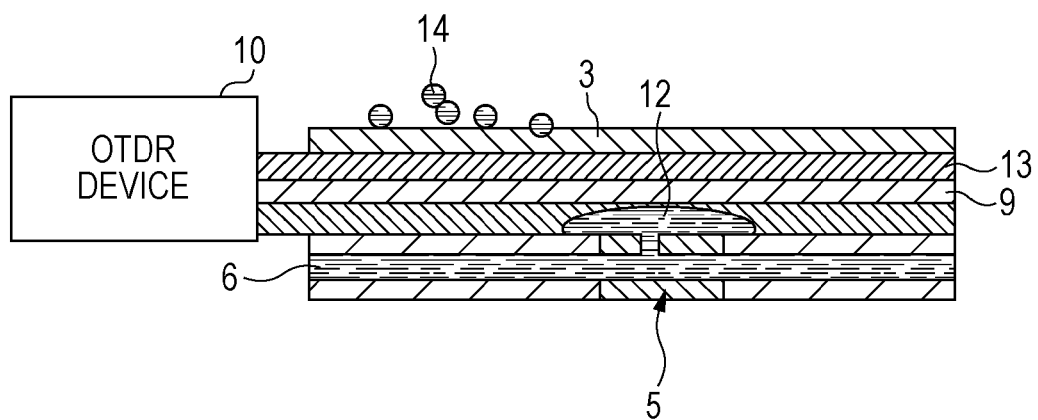
FIG. 4 is a schematic diagram illustrating a configuration of the liquid leakage detector according to the first embodiment incorporating a PCF as a liquid detection unit, and a state in which leakage occurs.

Second Exemplary Configuration of Liquid Leakage Detector Incorporating Optical Unit FIG. 4 is an example of the liquid leakage detector according to the first embodiment which incorporates an optical unit as a liquid detection unit as in the exemplary configuration illustrated in FIG. 3. The liquid leakage detector illustrated in FIG. 4 can detect, in addition to an electrically conductive liquid, a non-electrically conductive liquid, an oil-based liquid, solvent ink and an inflammable liquid. As illustrated in FIG. 4, a liquid detection unit 1, including a single PCF 9, is fixed to an area near a site with a possibility of liquid leakage 5 and is covered with a liquid impermeable member 3. The PCF 9 includes a cladding 13 and both ends of the PCF 9 are optically connected to the light source (not illustrated) which constitutes the light emitting unit and an OTDR device 10 which constitutes the light receiving unit. The PCF 9 is covered with the liquid impermeable member 3.

Operation for Leakage Detection

An operation for leakage detection in the liquid transport apparatus incorporating the liquid leakage detector of the configuration illustrated in FIG. 4 will be described in detail.

The OTDR device 10 as a measuring unit optically connected to the PCF 9 measures light propagation loss in the PCF 9 constantly or periodically. Upon occurrence of leakage, the leaked liquid 12 comes into contact with the PCF 9 and thereby propagation loss in PCF 9 increases. Upon detection of an increase in propagation loss in the PCF 9, the control unit determines that a liquid is leaking (i.e., waste water is leaking). Measurement of a distribution of propagation loss in the direction of a light beam path by the OTDR device 10 can also detect a site of leakage in addition to the existence of waste water leakage.

In a case in which no waste water leakage occurs but the adhesive droplets 14 (here, dewing droplet 14) adhere to the site with a possibility of liquid leakage 5, adhesion of the droplets to the cladding 13 is prevented by the liquid impermeable member 3 and thus propagation loss does not increase in the PCF 9. Thus, the control unit does not make false detection of the waste water leakage.

The liquid leakage detector illustrated in FIG. 4 can prevent false detection of the waste water leakage and detect waste water leakage correctly. The liquid leakage detector of the present embodiment can provide a liquid transport apparatus which achieves a stable operation without any interruption of liquid transfer due to false detection of the waste water leakage.

Figure 7:
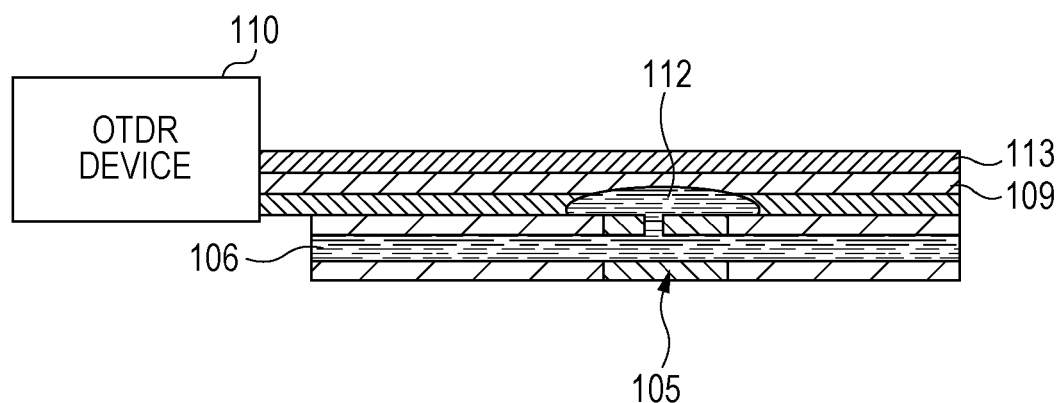
FIG. 7 is a schematic diagram illustrating a configuration of a related art liquid leakage detector incorporating an optical unit as a liquid detection unit, and a state in which leakage occurs.
Figure 8:
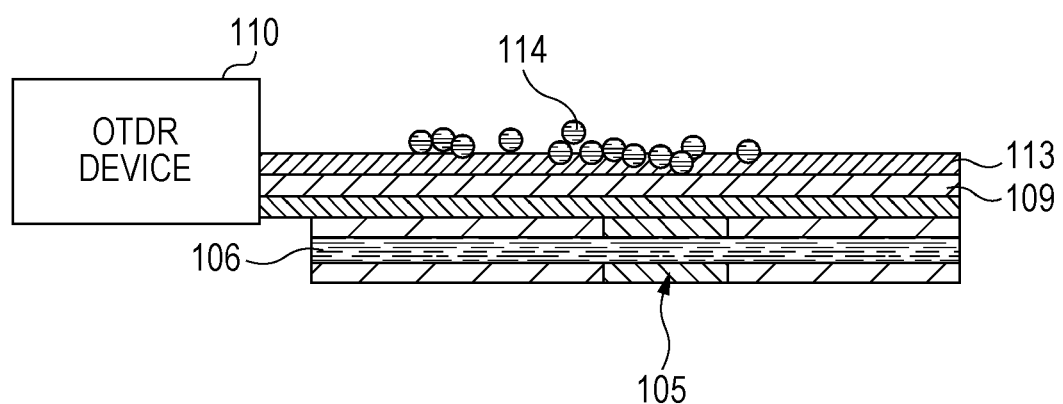
FIG. 8 is a schematic diagram illustrating a configuration of a related art liquid leakage detector incorporating a PCF as a liquid detection unit, and a state in which droplet adhesion occurs.

FIG. 7 is a schematic diagram of a related art liquid leakage detector incorporating a PCF and used for contaminated waste water pipe. As illustrated in FIG. 7, the related art liquid leakage detector can detect leakage by the OTDR device 110 when the leakage occurs at a site with a possibility of liquid leakage 105 and the waste water comes into contact with the PCF 109. The related art liquid leakage detector, however, is not provided with a liquid impermeable member 103 which covers the PCF 109; thus in a state in which no leakage occurs actually but dewing droplets 114 adhere to the PCF 109, false detection of the occurrence of leakage will be made.

Although the exemplary configurations according to the first embodiment incorporating electrical and optical liquid detection units have been described, the liquid detection unit is not limited to the same. For example, the liquid detection unit may use an absorber which chemically reacts with the liquid or may photograph color changes or temperature changes of the absorber with a camera and performs image recognition to detect the liquid. With these methods, the configuration according to the first embodiment can prevent false detection and make correct leakage detection.

Next, a liquid leakage detector according to a second embodiment will be described.

The liquid leakage detector according to the second embodiment includes a first liquid detection unit and a second liquid detection unit. The first liquid detection unit is the liquid detection unit according to the first embodiment. The second liquid detection unit is situated adjacent to the first liquid detection unit and detects droplets adhering to a site with a possibility of droplet adhesion exposed to the ambient air. The liquid leakage detector further includes a determination unit which determines whether at least one of liquid leakage and droplet adhesion is occurring in response to signals from the first liquid detection unit and the second liquid detection unit.

The first liquid detection unit detects the leaked liquid and the second liquid detection unit may detect only the adhesive droplets. The site, with a possibility of droplet adhesion detected by the second liquid detection unit, is situated near the site with a possibility of liquid leakage 5 detected by the first liquid detection unit. The present embodiment, which is further provided with the second liquid detection unit in addition to the first liquid detection unit, can detect the leaked liquid and the adhesive droplets separately. For example, the inkjet printer incorporating the liquid leakage detector according to the second embodiment can also detect ink mist in addition to ink leakage. With this configuration, leakage from an ink path and deposition of ink mist can be monitored at the same time and, therefore, partial corrosion of the inkjet printer and dropping of ink on the printed matter caused by deposition of ink mist can be prevented.

Figure 9:
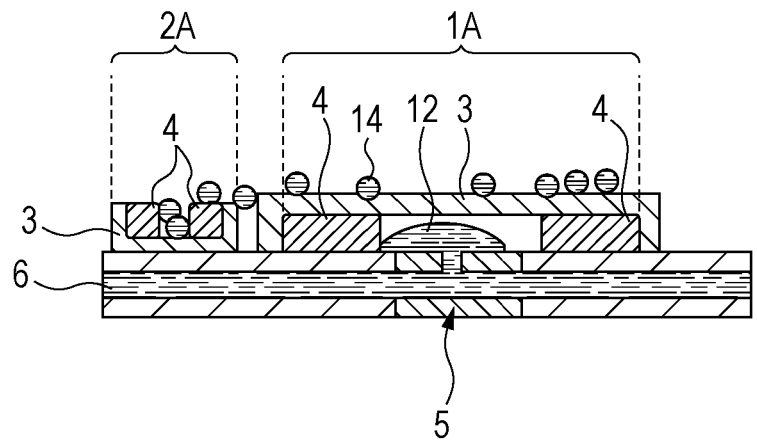
FIG. 9 is a schematic diagram illustrating a configuration of a liquid leakage detector according to a second embodiment incorporating an electrical unit as a liquid detection unit, and a state in which leakage occurs.

Exemplary Configuration of Liquid Leakage Detector Incorporating Electrical Unit FIG. 9 is a schematic diagram of an example of a liquid leakage detector for detecting an electrically conductive liquid 6 in the pipe according to the second embodiment. In the liquid leakage detector for detecting an electrically conductive liquid according to the present embodiment, as illustrated in FIG. 9, a first liquid detection unit 1A as the first liquid detection unit includes a pair of electrodes 4 which is fixed to an area near the site with a possibility of liquid leakage 5 and is covered with a liquid impermeable member 3. A second liquid detection unit 2A includes a pair of electrodes 4 which is fixed to an area near the site with a possibility of liquid leakage 5 via the liquid impermeable member 3 and is exposed to the ambient air. In the present embodiment, the configurations of the liquid impermeable member 3, the electrodes 4 and the site with a possibility of liquid leakage 5 are the same as those illustrated in FIG. 1 and description thereof will be omitted.

Operation for Leakage Detection

An operation for leakage detection in an inkjet printer incorporating the liquid leakage detector of the configuration illustrated in FIG. 9 will be described in detail. When a liquid (i.e., ink) leaks from the site with a possibility of liquid leakage 5 as illustrated in FIG. 9, the leaked liquid 12 spreads between the pair of electrodes 4 and forms an electrical conductive path and thus the electrical resistance between the pair of electrodes 4 may be lowered. The control unit determines that ink leakage has occurred upon detection of lowered electrical resistance in the first liquid detection unit 1.

If no ink leakage occurs but ink mist adheres to and deposits on the site with a possibility of liquid leakage 5, entering of ink between the pair of electrodes 4 is prevented by the liquid impermeable member 3; there is therefore no change in electrical resistance between the electrodes 4 in the first liquid detection unit 1A. In the second liquid detection unit 2A, however, electrical resistance between the pair of electrodes 4 is lowered. The control unit determines that ink mist adheres to the site with a possibility of liquid leakage 5 upon detection of lowered electrical resistance in the second liquid detection unit 2A.

The liquid leakage detector according to the present embodiment with the configuration described above not only can prevent false detection by adhesion of ink mist but can separately detect liquid leakage and adhesion of ink mist.

Figure 10:
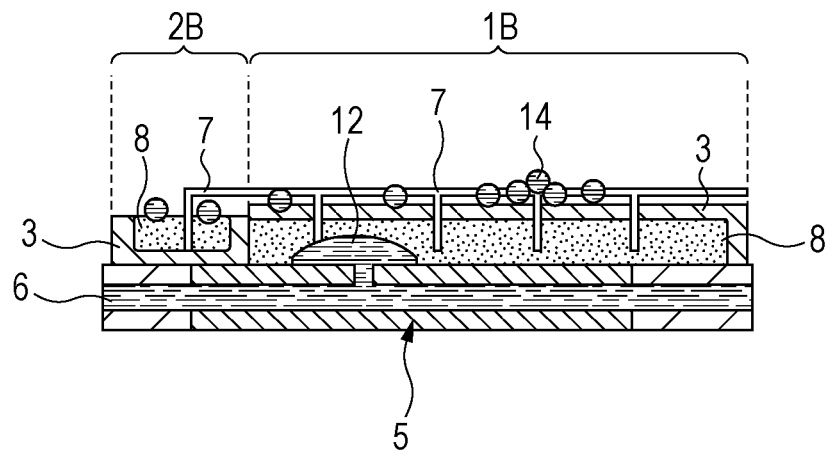
FIG. 10 is a schematic diagram illustrating a configuration of a liquid leakage detector according to the second embodiment incorporating an optical unit as a liquid detection unit, and a state in which leakage occurs.

Third Exemplary Configuration of Liquid Leakage Detector Incorporating Optical Unit FIG. 10 is an example of the liquid leakage detector according to the second embodiment, which is an exemplary configuration incorporating an optical unit as a liquid detection unit.

As illustrated in FIG. 10, a liquid leakage detector according to the present embodiment includes a first liquid detection unit 1B as a first liquid detection unit. The first liquid detection unit 1B is fixed to an area near a site with a possibility of liquid leakage 5 of a liquid pipe and is covered with a liquid impermeable member 3. In a second liquid detection unit 2B, one end of the optical fiber pair 7 is inserted in an absorber 8 which is exposed to the ambient air and is fixed, via the liquid impermeable member 3, to an area near the site with a possibility of liquid leakage 5. In the present embodiment, the configurations of the liquid detection unit 1, the liquid impermeable member 3, the site with a possibility of liquid leakage 5, the optical fiber pair 7 and the absorber 8 may be the same as those illustrated in FIG. 2, and description thereof will be omitted.

Operation for Leakage Detection

An operation for leakage detection in an inkjet printer incorporating the liquid leakage detector of the configuration illustrated in FIG. 10 will be described in detail. As illustrated in FIG. 10, if a liquid (i.e., ink) leaks from the site with a possibility of liquid leakage 5, the leaked ink is absorbed in the absorber 8 and thereby the amount of scattered light changes in the absorber 8 at an area near the optical fiber pair 7. For example, the amount of scattered light of a wavelength band which ink absorbs is reduced. The control unit determines that the ink has leaked upon detection of a reduction in the amount of scattered light in the first liquid detection unit 1B.

If no ink leakage occurs but ink mist adheres to and deposits on the site with a possibility of liquid leakage 5, since entering of ink into the absorber 8 is prevented by the liquid impermeable member 3 covering the absorber 8, the amount of scattered light from the optical fiber pair 7 does not change in the first liquid detection unit 1B. The amount of scattered light is reduced in the second liquid detection unit 2B. The control unit determines that ink mist adheres upon reduction in the amount of scattered light in the second liquid detection unit 2B.

The liquid leakage detector according to the present embodiment with the configuration described above not only can prevent false detection by adhesion of ink mist but separately detect ink leakage and adhesion of ink mist.

Figure 11:
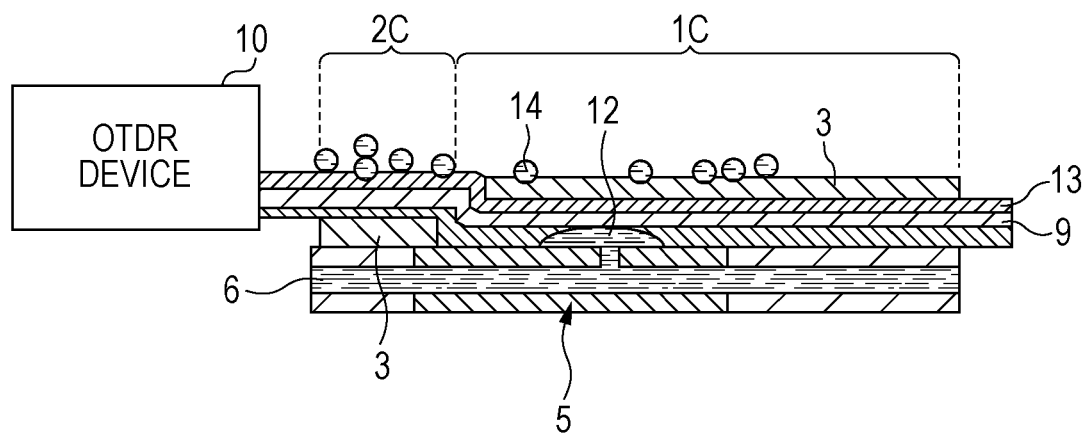
FIG. 11 is a schematic diagram illustrating a configuration of a liquid leakage detector according to the second embodiment incorporating a PCF as a liquid detection unit, and a state in which leakage occurs.

Fourth Exemplary Configuration of Liquid Leakage Detector Incorporating Optical Unit FIG. 11 is an example of the liquid leakage detector according to the second embodiment, which is an exemplary configuration incorporating a PCF as a liquid detection unit.

As illustrated in FIG. 11, a liquid leakage detector according to the embodiment includes a first liquid detection unit 1C. The first liquid detection unit 1C is constituted by a single PCF 9 fixed to an area near a site with a possibility of liquid leakage 5 and is covered with a liquid impermeable member 3. The second liquid detection unit 2C shares the PCF 9 with the first liquid detection unit 1C and is fixed to an area near the site with a possibility of liquid leakage 5 via the liquid impermeable member 3. In the present embodiment, the configurations of the liquid impermeable member 3, the electrodes 4, the site with a possibility of liquid leakage 5 and the PCF 9 are the same as those illustrated in FIG. 4 and description thereof will be omitted.

Operation for Leakage Detection

An operation for leakage detection in a waste water transport apparatus incorporating the liquid leakage detector of the configuration illustrated in FIG. 11 will be described in detail.

If the waste water leaks from the site with a possibility of liquid leakage 5, the waste water comes into contact with the PCF 9 and thereby propagation loss in the PCF 9 increases. With this change, a distribution of propagation loss in the length direction of a light beam path is measured by the OTDR device 10. The control unit determines that waste water has leaked upon detection of an increase in the propagation loss in the first liquid detection unit 1C. It is also possible to detect a site of leakage based on the distribution of propagation loss in the PCF 9.

In a case in which no waste water has leaked but dew condensation has occurred on a surface of the liquid pipe, since adhesion of the adhesive droplets 14 to the cladding 13 is prevented by the liquid impermeable member 3, propagation loss does not increase in the PCF 9 of the first liquid detection unit 1C. However, propagation loss increases in the second liquid detection unit 2C. Thus, if the propagation loss does not increase in the first liquid detection unit 1C but increases in the second liquid detection unit 2C, the control unit determines that the droplets have adhered to the outside of the liquid pipe which is the liquid path.

The liquid leakage detector according to the present embodiment with the configuration described above not only can prevent false detection by adhesion of adhesive droplets 14 but can separately detect leakage of waste water and adhesion of droplets.

Example of Application to Inkjet Printer

Figure 12:
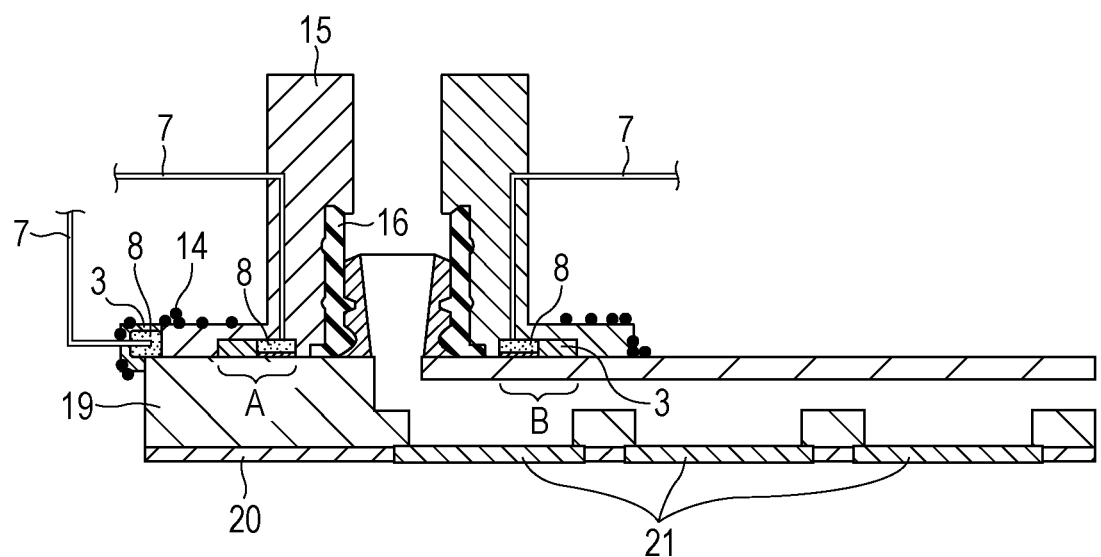
FIG. 12 is a schematic sectional view of an inkjet printer to which the liquid leakage detector illustrated in FIG. 2 is attached near a recording head.

FIG. 12 is a sectional view illustrating an example of an inkjet printer according to the invention in which the liquid leakage detector of the configuration illustrated in FIG. 2 is attached at an area near the recording heads. Nozzle tips 21 which have a function to eject ink are fixed to a nozzle tip support 19 and are electrically connected to a flexible circuit board 20. Ink is supplied to the nozzle tips 21 via ink paths provided in the nozzle tip support 19. The nozzle tips 21 eject ink through predetermined nozzles at predetermined timing in response to electrical signals from the flexible circuit board 20.

Joint portions of the liquid path member 15 and the nozzle tip support 19 are sites with a possibility of leakage due to, for example, degradation of a rubber member 16 which is a sealing unit and wrong attachment of the member. In a case in which the liquid leakage detector according to the embodiment is provided at such joint portions, the liquid leakage detector may be situated not only an outside of the liquid path member 15 (i.e., the leftmost place at which liquid leakage detector is situated in FIG. 12) but inside the liquid path member 15 (i.e., a site A and a site B in FIG. 12). If the liquid leakage detector is situated in this manner, the leaked liquid can be detected promptly. In a case in which no liquid leakage has occurred but adhesive droplets (in this case, ink mist) 14 adhere to and deposit on the joint portions, entering of the ink mist into the absorber 8 is prevented by the liquid impermeable member 3 and the liquid path member 15, and no false detection of ink leakage will be made.

Figure 13:
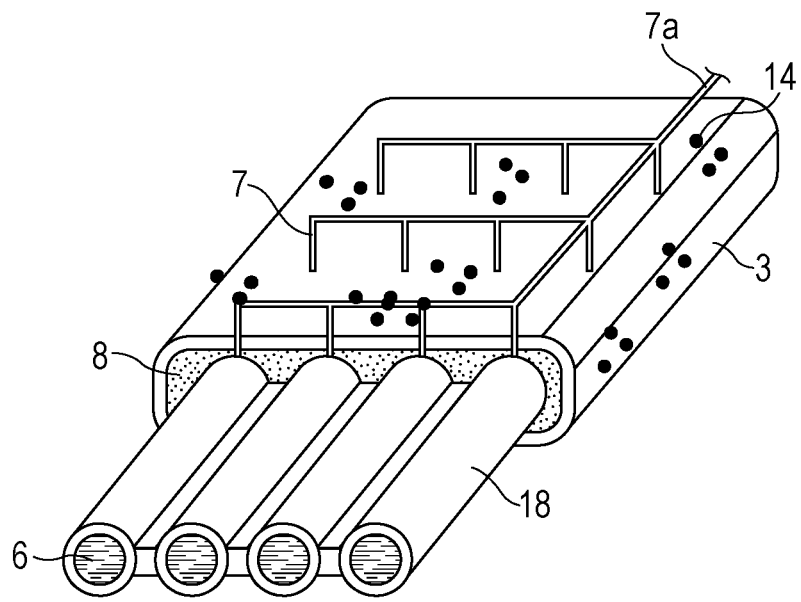
FIG. 13 is a schematic diagram illustrating an ink tube unit of an inkjet printer to which the liquid leakage detector illustrated in FIG. 2 is attached.

FIG. 13 is a perspective view of an example of an embodiment in which the liquid leakage detector of the constitution illustrated in FIG. 2 is attached to the ink tubes which connect the recording heads and the ink tank of an off-carriage inkjet printer. The configuration illustrated in FIG. 13 includes four ink tubes 18 corresponding to 4 colors (CMYK). The ink tubes 18 are bundled together. The ink tubes 18 are wrapped with the liquid impermeable member 3 and the absorber 8 on their outer circumference. One end of each of the optical fiber pairs 7 is embedded at a plurality of sites in the absorber 8.

In the event that ink leaks from the ink tubes 18, a part of the leaked ink is absorbed in the absorber 8 and the leakage is detected by the optical fiber pairs 7 embedded in the absorber 8. Since a plurality of optical fiber pairs 7 are provided in the absorber 8, the optical fiber pairs 7 not only can detect the existence of leakage but can detect a site of leakage and a leakage rate in response to signals from each of the optical fiber pairs 7 and with reference to the temporal change in the signals. In a case in which no leakage has occurred but adhesive droplets (in this case, ink mist) 14 adhere to and deposit on the joint portions, contact between the ink mist and the absorber 8 is prevented by the liquid impermeable member 3 and thus no false detection of ink leakage will be made.

Although the configuration illustrated in FIG. 13 includes a ring-shaped liquid leakage detector, a sheet-shaped or strip-shaped liquid leakage detector may be provided to wrap the ink tubes 18. With this configuration, the ink tubes 18 and the absorber 8 can be replaced easily after the detection of the leakage and thereby reduce time and effort regarding leakage monitoring.

Figure 14:
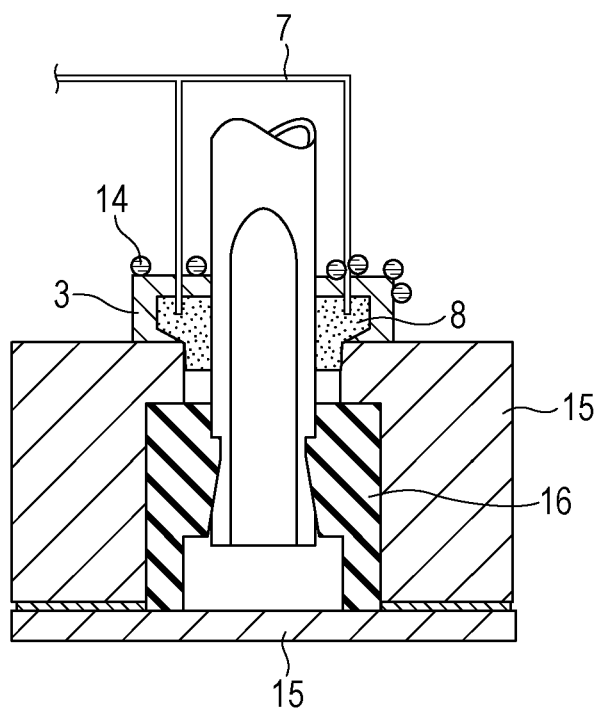
FIG. 14 is a schematic sectional view of an area near a connector of an ink tube to which the liquid leakage detector illustrated in FIG. 2 is attached.

FIG. 14 is an example of an embodiment in which the liquid leakage detector of the configuration illustrated in FIG. 2 is attached to an area near a connecting portion of the ink tubes 18 illustrated in FIG. 13 to, for example, the ink tank and a filter box. The liquid impermeable member 3 and the absorber 8 are provided as a ring around the ink tubes 18 which are in contact with a connector. When leakage occurs within the connector, a part of the leaked ink is absorbed in the absorber 8 and the leakage is detected by the optical fiber pairs 7 embedded in the absorber 8. Since the absorber 8 is separated from the adhesive droplets (in this case, ink mist) 14 by the liquid impermeable member 3, no false detection of ink leakage will be made in a case in which no leakage occurs but the ink mist adheres to and deposit on the joint portion.

Although the optical fiber pairs 7 in FIG. 13 are illustrated to branch from a single optical fiber, the optical fiber pairs 7 are bundled together to provide a portion 7a and each pair is optically connected to the photodetector independently.

Next, a liquid transport apparatus according to a third embodiment will be described.

The liquid transport apparatus according to the third embodiment includes a liquid storage unit, a liquid outlet unit, a liquid path and a liquid transfer pump. The liquid path provides a means for the liquid storage unit and the liquid outlet unit to communicate with each other. The liquid transfer pump functions as a liquid transfer unit which pressurizes the gas component in the liquid path or in the liquid storage unit. The liquid transport apparatus includes the liquid leakage detector according to the first or second embodiment provided on a surface of any one of the liquid storage unit, the liquid outlet unit and the liquid path. The liquid transport apparatus also includes a pressure-reducing mechanism and a control unit. The pressure-reducing mechanism reduces the pressure of the gas component in the liquid path or in the liquid storage unit to the pressure lower than the atmospheric pressure. The control unit activates, i.e., turns on the pressure-reducing mechanism when the liquid leakage detector detects liquid leakage.

Figure 15:
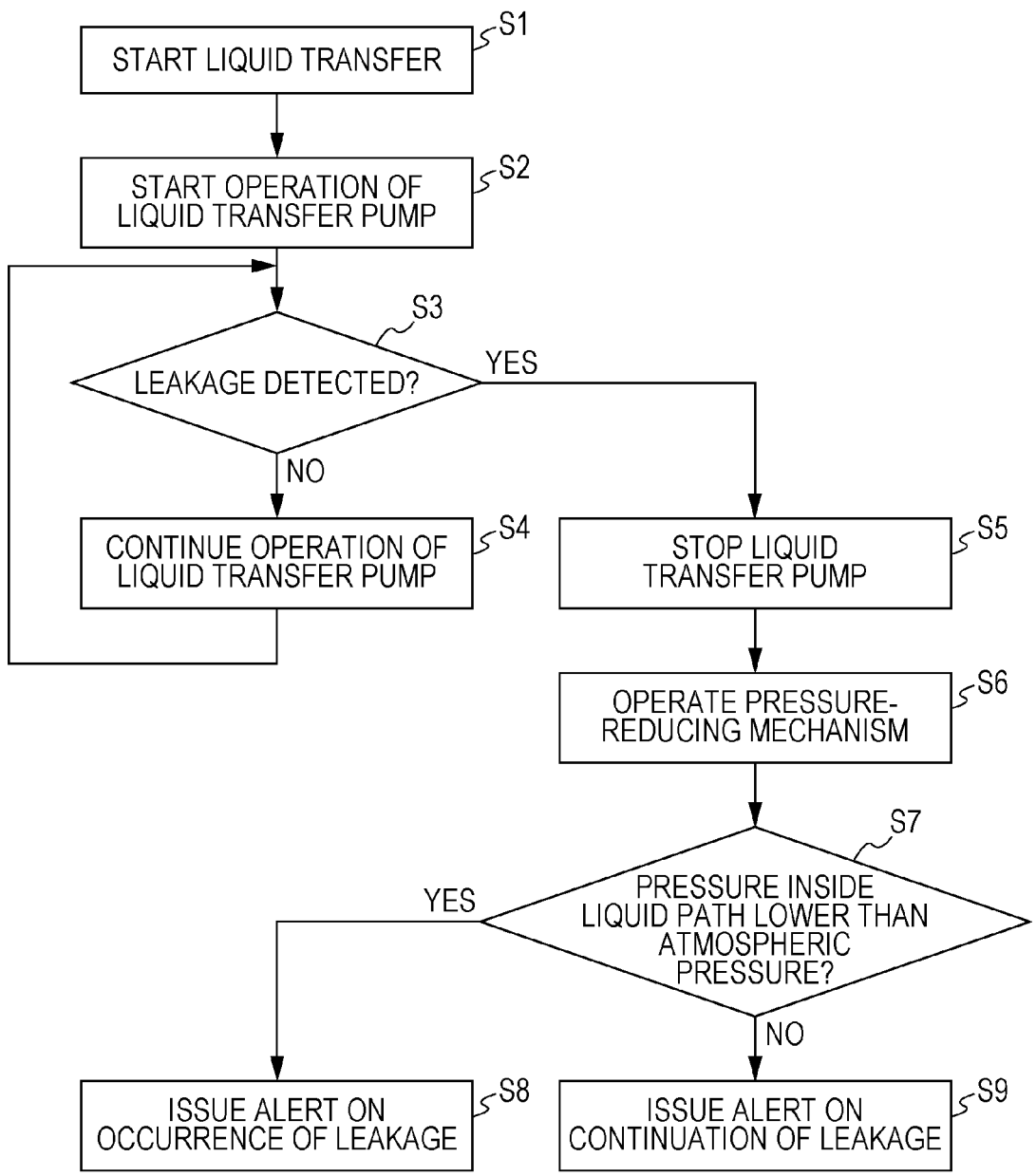
FIG. 15 is a flowchart of a part of an operation of a control unit in the liquid transport apparatus according to the embodiments.

FIG. 15 is an example of a flowchart of an operation of the control unit in the liquid transport apparatus according to the third embodiment. As illustrated in FIG. 15, when the liquid transfer is started (Step S1), the liquid transport apparatus is powered on and the operation of the liquid transfer pump is started to start liquid transfer (Step S2). At the same time as the start of the operation of the liquid transfer pump, signals from the liquid leakage detector are monitored to determine whether liquid leakage has been detected (Step S3). If no liquid leakage is detected, the control unit continues operating the liquid transfer pump (Step S4). If liquid leakage is detected, the control unit promptly stops the liquid transfer pump (Step S5) and activates, i.e., turns on the pressure-reducing mechanism (Step S6) so as to let the pressure of the gas component inside the liquid path be less than atmospheric pressure.

Then, the control unit determines whether the internal pressure of the liquid path has been reduced to the pressure lower than atmospheric pressure using a manometer provided inside the liquid path (Step S7). When it is determined that the internal pressure of the liquid path has been reduced, the control unit issues an alert to notify the user of the occurrence of leakage (Step S8). In the event that an abnormality is detected in the pressure-reducing mechanism and the internal pressure of the liquid path has not been reduced, it is considered that the leakage is continued; thus the control unit issues an alert to notify the user of the continuation of leakage (Step S9).

As described above, since the internal pressure of the liquid path is automatically reduced upon detection of leakage, continued leakage from the liquid path or the liquid storage unit can be prevented. It is therefore possible to significantly reduce damage, which is caused by the scattering of the leaked liquid, to the liquid transport apparatus and the surrounding of the apparatus. It is further possible to help the user determine what action should be taken in response to the notification with different alerts indicating the state in which the leakage has been stopped and the state in which the leakage continues.

If the liquid leakage detector can also detect a site of leakage and a leakage rate, notifications regarding, for example, the site of leakage, the leakage rate and the amount of leakage may also be added to the alert. If the user is notified of such information by, for example, a display, the user can precisely determine what action should be taken. Here, the amount of leakage is an estimated value obtained by integrating the time required after the leakage is detected until the internal pressure of the liquid path is determined to be reduced and the leakage rate.

Process for Determination of Leakage

Figure 16:
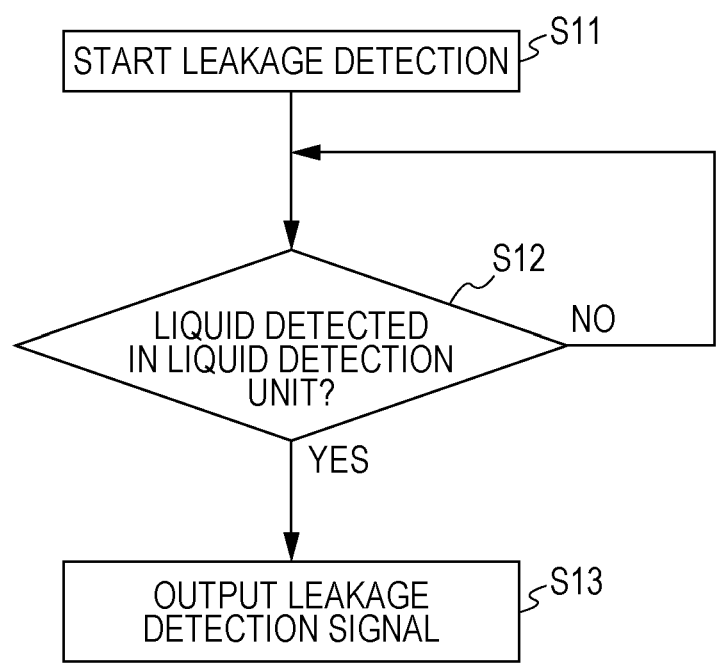
FIG. 16 is a flowchart of an example of a process performed by the control unit to determine the existence of leakage in an inkjet printer incorporating the liquid leakage detector illustrated in FIG. 1.

FIG. 16 is an example of a flowchart for determination of leakage made by the control unit in the inkjet printer incorporating the liquid leakage detector illustrated in FIG. 1. The process of the flowchart of FIG. 16 is suitable for liquid leakage detectors which detect only the existence of the liquid, such as the liquid leakage detector incorporating the electrical unit as the first liquid detection unit. As illustrated in FIG. 16, after the leakage detection is started (Step S11), it is determined whether a liquid has been detected by the liquid detection unit 1A (Step S12). If a liquid is detected by the liquid detection unit 1A, the control unit determines that leakage has occurred and outputs a leakage detection signal (Step S13). If no liquid is detected by the liquid detection unit 1A, detection state is continued.

Figure 17:
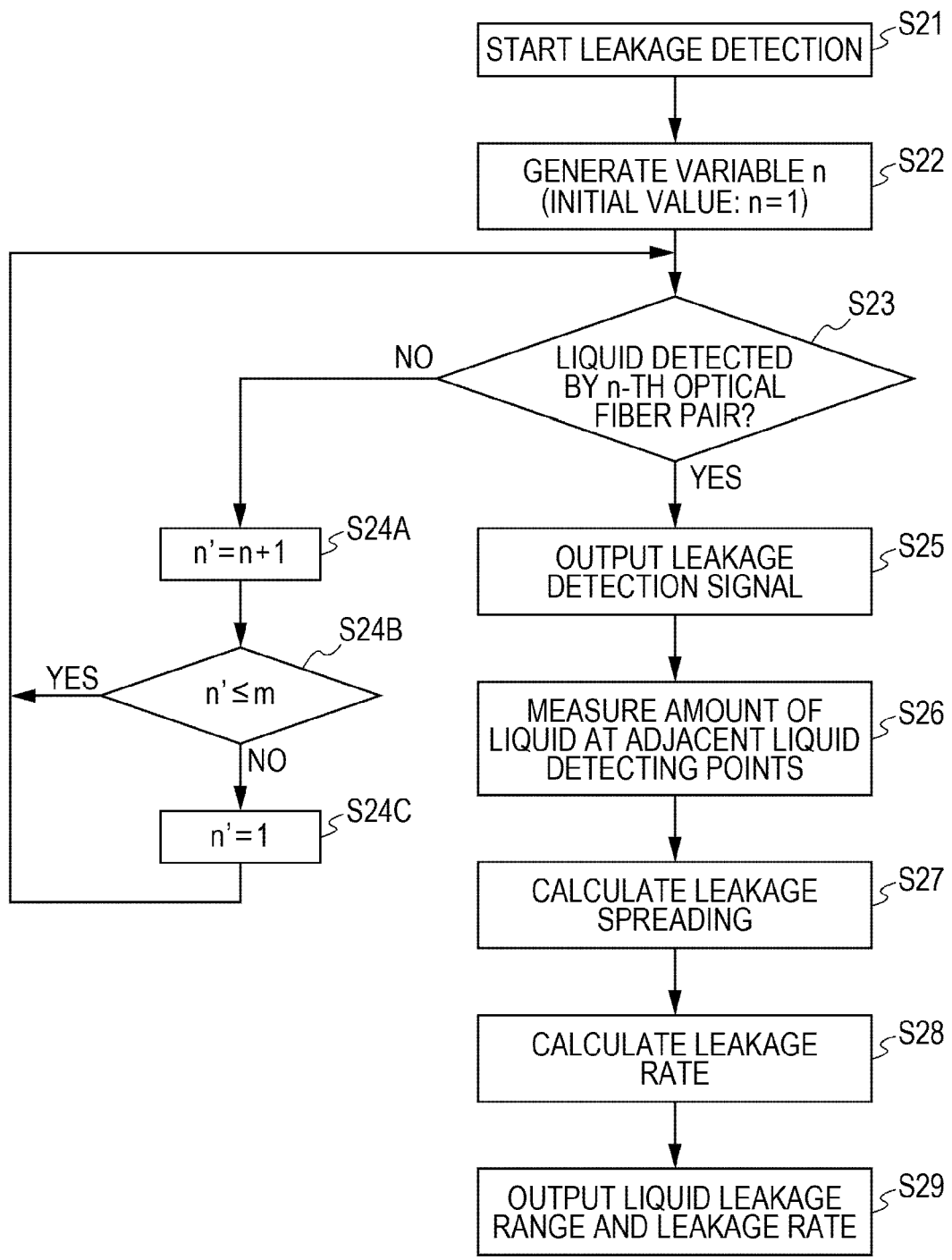
FIG. 17 is a flowchart of an example of a process performed by the control unit to determine the existence of leakage in an inkjet printer incorporating the liquid leakage detector illustrated in FIG. 2.

FIG. 17 is an example of a flowchart for the determination of leakage made by the control unit in a waste water transport apparatus as the liquid transport apparatus incorporating the liquid leakage detector illustrated in FIG. 2. The process illustrated in FIG. 17 is suitable for liquid leakage detectors which can detect, for example, a site of leakage, leakage spreading and a spreading speed, such as the liquid leakage detector having a plurality of liquid detecting points illustrated in FIG. 2.

In the process illustrated in FIG. 17, the liquid leakage detector having m liquid detecting points is used. As illustrated in FIG. 17, after the leakage detection is started (Step S21), the control unit generates a variable n of which initial value being set to "1" (Step S22) and then determines whether a liquid has been detected by the n-th optical fiber pair of the liquid leakage detector (Step S23). If no liquid is detected by the n-th optical fiber pair of the liquid leakage detector, the existence of a liquid in the n-th optical fiber pair of the liquid leakage detector is sequentially detected regarding the first to the m-th liquid detecting points (Steps S24A, S24B and S24C). If no leakage is detected after the m-th liquid detecting point is detected, the process repeats the process of detecting the first to the m-th liquid detecting points. If a liquid is detected at the n-th liquid detecting point, the control unit outputs a leakage detection signal (Step S25). At the same time, the amount of the liquid at the liquid detecting point at which the liquid has been detected and at the liquid detecting point adjacent to that point are measured (Step S26) and then the amount of leakage, the site of leakage and the leakage spreading are computed from the amount of the liquid at each of these liquid detecting points (Step S27). The leakage rate is computed from the change in the leakage spreading and the spreading time (Step S28) and then the range of the leakage and the leakage rate are output (Step S29). In this manner, since the user is notified of the occurrence of leakage and additional information about the leaking condition is output, the user can determine what action should be taken further precisely.

Figure 18:
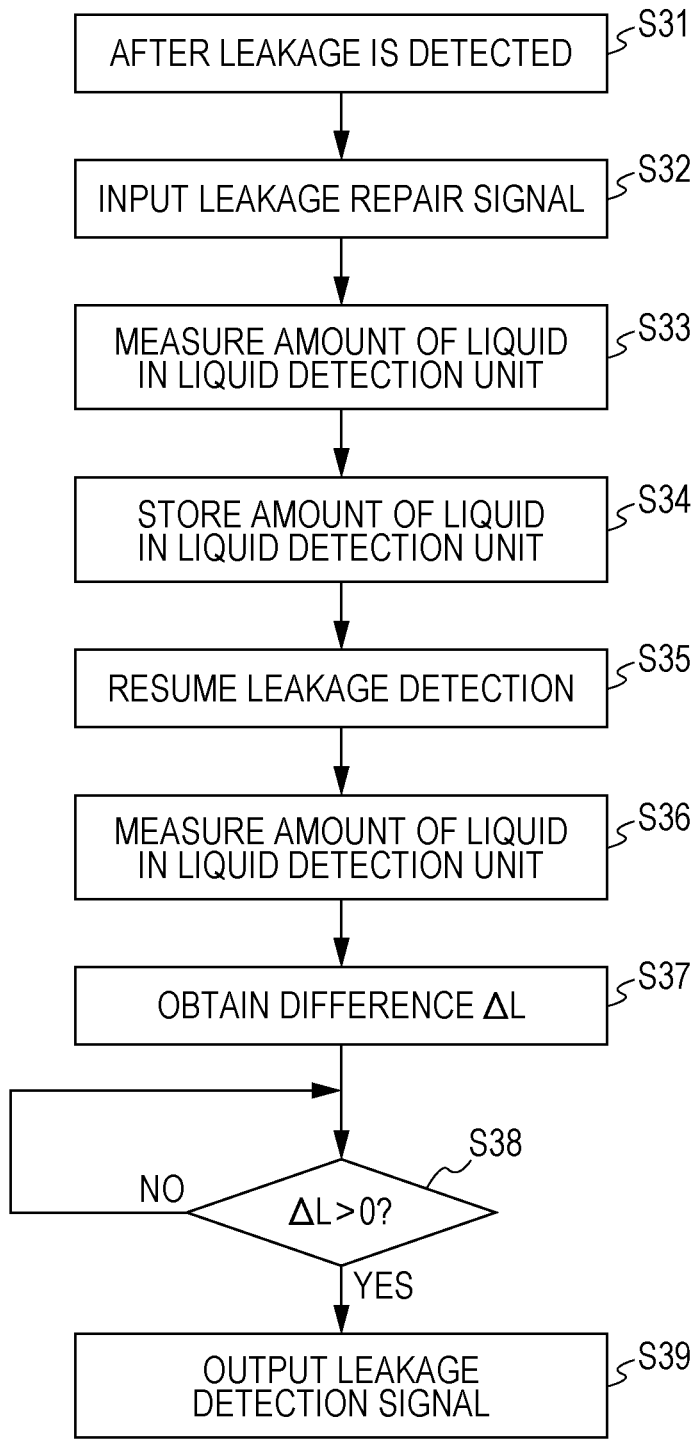
FIG. 18 is a flowchart of an example of a process performed by the control unit to determine the existence of leakage in a waste water transport apparatus incorporating the liquid leakage detector illustrated in FIG. 6.

FIG. 18 is a flowchart of an example of a process performed by the control unit to determine the existence of leakage when leakage monitoring is resumed after the repair of the leakage in a waste water transport apparatus as the liquid transport apparatus incorporating the liquid leakage detector illustrated in FIG. 2. The process illustrated in FIG. 18 is suitable for liquid leakage detectors which can measure the amount of liquid in the liquid detection unit, such as the liquid leakage detector illustrated in FIG. 2. If the control unit performs such a process, leakage monitoring can be resumed without any replacement of components, such as the absorber after the leakage is detected.

As illustrated in FIG. 18, after leakage is detected (Step S31), if the user repaired the leakage, a leakage repair signal is input by the user (Step S32). At this time, the control unit first computes the amount of the liquid in the absorber of the liquid detection unit 1B (Step S33). Then the control unit stores the computed amount of the liquid in internal storage (Step S34) and resumes the leakage monitoring (Step S35). Although not illustrated, if the amount of the liquid in the absorber cannot be measured due to any abnormalities occurring in the liquid detection unit 1B, it is also possible not to resume the leakage monitoring and to output a signal indicating an abnormality is occurring. With this, self-diagnostics of the detection function is performed at the time of resumption of the leakage monitoring. As a result, reliability in the detection function is enhanced.

Next, after the resumption of the leakage monitoring, the control unit computes the amount of the liquid in the liquid detection unit 1B (Step S36) and computes a difference $\Delta L$ by subtracting the stored amount of the liquid from the computed amount of the liquid (Step S37). Subsequently, the control unit determines whether $\Delta L>0$ is satisfied (Step S38). Satisfaction of $\Delta L>0$ indicates that the liquid further leaked in the liquid detection unit after the resumption of the leakage monitoring; thus the control unit determines that leakage has occurred and outputs a leakage detection signal (Step S39).

Similarly, in the liquid leakage detectors incorporating the first and second liquid detection units are used, when adhesion of a liquid or droplets is detected in the first and second liquid detection units, the amount of the liquid may be stored in the internal storage as described above. Also in this configuration, the control unit makes detection in accordance with $\Delta L$ obtained by subtracting the amount of the liquid stored in the internal storage from the amount of the liquid detected afterward in the first and second liquid detection units.

Figure 19:
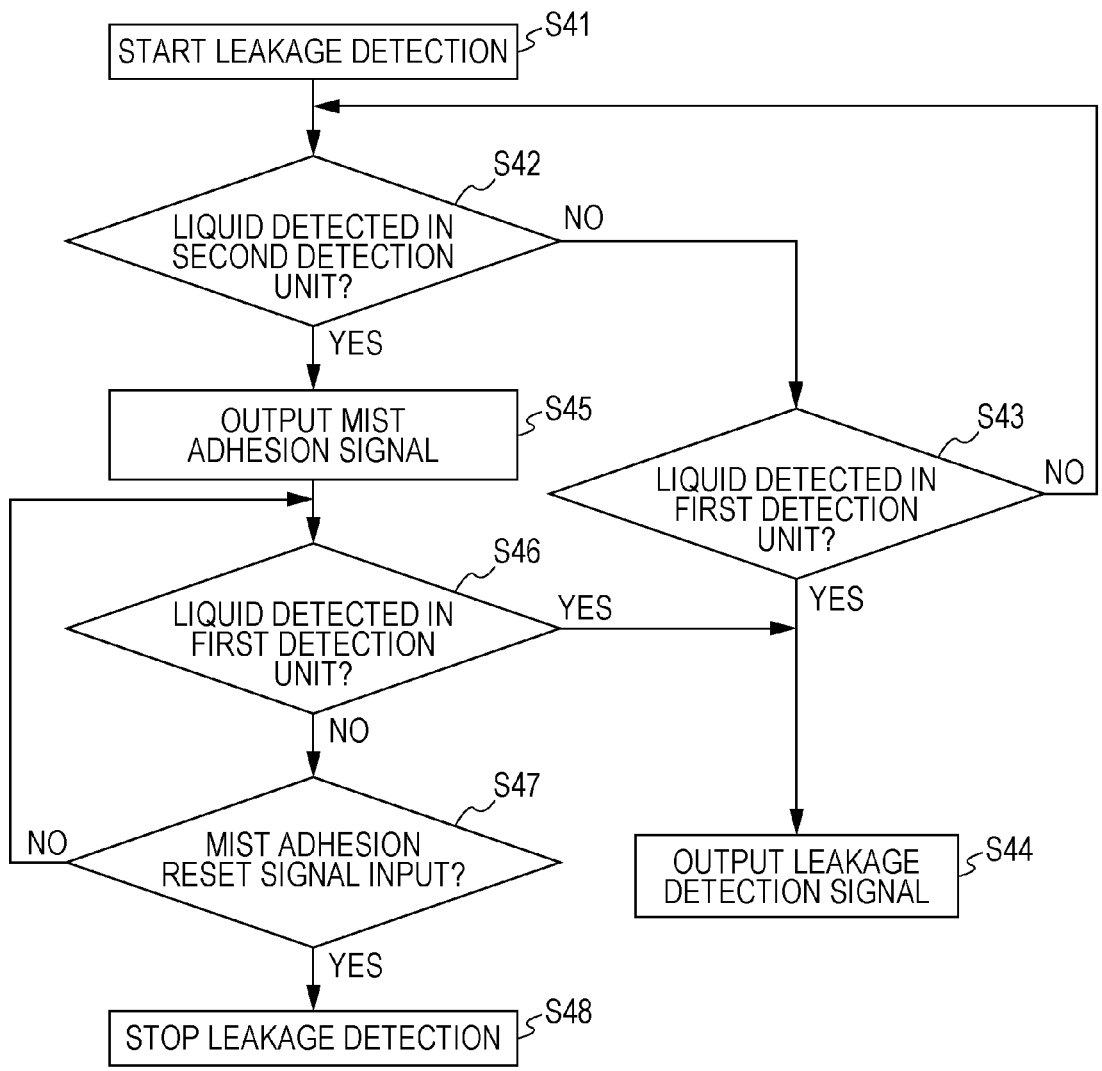
FIG. 19 is a flowchart of an example of a process performed by the control unit to determine the existence of leakage when leakage monitoring is resumed after the repair of a leakage site in a waste water transport apparatus incorporating the liquid leakage detector illustrated in FIG. 2.

FIG. 19 is an example of a flowchart of a process performed by the control unit in an inkjet printer incorporating the liquid leakage detector illustrated in FIG. 10. In the flowchart of FIG. 19, after the leakage detection is started (Step S41), the control unit monitors the signal from the second liquid detection unit 2B and determines whether a liquid has been detected in the second liquid detection unit 2B (Step S42). If no droplets are detected in the second liquid detection unit 2B, the control unit monitors the signal from the first liquid detection unit 1B and determines whether a liquid has been detected in the first liquid detection unit 1B (Step S43).

If the liquid is detected by the first liquid detection unit 1B, the control unit outputs a leakage detection signal (Step S44). If no liquid is detected by the first liquid detection unit 1B, the second liquid detection unit 2B again detects droplets.

If droplets are detected by the second liquid detection unit 2B, the control unit determines that adhesion of the ink mist has occurred and outputs a mist adhesion signal (Step S45). Then the control unit monitors the signal from the first liquid detection unit 1B and determines whether a liquid has been detected in the first liquid detection unit 1B (Step S46). If a liquid is detected in the first liquid detection unit 1B, the control unit outputs a leakage detection signal (Step S44). If no liquid is detected in the first liquid detection unit 1B, the control unit detects the existence of input of a mist adhesion reset signal and determines whether the mist adhesion reset signal has been input (Step S47). If the mist adhesion reset signal is input, the control unit determines that the user has been notified of the mist adhesion signal and stops the leakage detection (Step S48). If no mist adhesion reset signal is input, the control unit determines that the user does not stay near the apparatus and thus is not notified of the mist adhesion signal, and continues the leakage monitoring. Thus, the leakage monitoring in the first liquid detection unit is continued until the user inputs the reset signal. With such a process flow, the leakage monitoring can be continued even if the user does not stay near the apparatus after the adhesion of ink mist is detected.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-181768 filed Aug. 16, 2010, which is hereby incorporated by reference herein in its entirety.

What is claimed is:

1. A liquid leakage detector comprising:
   a first liquid detection unit provided at a member to be detected, the first liquid detection unit being configured to detect a liquid leaked from the member to be detected;
   a liquid impermeable member which covers the first liquid detection unit to protect the same from the ambient air; and
   a determining unit configured to determine whether the liquid is leaking from the member to be detected in response to a signal from the first liquid detection unit,
   wherein the first liquid detection unit includes:
   a measuring unit configured to include a light emitting unit and a light receiving unit; and
   an optical fiber pair which includes a light guiding optical fiber and a light receiving optical fiber, one end of the light guiding optical fiber being disposed inside an absorber, the other end of the light guiding optical fiber being optically connected to the light emitting unit, one end of the light receiving optical fiber being disposed inside the absorber and the other end being is optically connected to the light receiving unit,
   wherein the change in an optical property in the absorber is measured by letting light from the light emitting unit be emitted from the one end of the light guiding optical fiber and letting light entering from the one end of the light receiving optical fiber be received by the light receiving unit.

2. The liquid leakage detector according to claim 1, further comprising a second liquid detection unit provided adjacent to the first liquid detection unit and exposed to the ambient air, the second liquid detection unit being configured to detect droplets.

3. The liquid leakage detector according to claim 2, wherein the first liquid detection unit or the second liquid detection unit is configured to include a pair of electrodes arranged on both sides of a gap.

4. The liquid leakage detector according to claim 2, wherein the first liquid detection unit or the second liquid detection unit includes an absorber which produces a change in an optical property by absorbing a liquid and a measuring unit configured to measures the change in the optical property of the absorber.

5. A method of detecting liquid leakage in which liquid leakage is detected using the liquid leakage detector according to claim 2, the method comprising a step of determining whether liquid leakage has occurred in response to a signal from the first liquid detection unit or the second liquid detection unit.

6. A method of detecting liquid leakage in which liquid leakage from a liquid path is detected using the liquid leakage detector according to claim 2, the method comprising:
   a step of determining the existence of liquid leakage in response to a signal from the first liquid detection unit;

a step of determining the existence of adhesion of droplets adhesion in response to a signal from the second liquid detection unit; and a step of determining that a liquid has adhered from outside the liquid path when no liquid leakage occurs in the first liquid detection unit and adhesion of the droplets occurs in the second liquid detection unit.

7. The liquid leakage detector according to claim 1, wherein the change in the optical property is a change in an amount of scattered light.

8. The liquid leakage detector according to claim 1, wherein the first liquid detection unit or the second liquid detection unit includes at least two optical fiber pairs.

9. A liquid transport apparatus which includes a liquid storage unit, a liquid outlet unit, a liquid path which lets the liquid storage unit and the liquid outlet unit communicate with each other, and a liquid transfer unit configured to supply a liquid from the liquid storage unit to the liquid outlet unit, the apparatus comprising:

the liquid leakage detector according to claim 1, provided on a surface or a connecting portion of one of the liquid storage unit, the liquid outlet unit, the liquid path, or the liquid transfer unit;

a pressure-reducing mechanism which reduces internal pressure of the liquid path or the liquid storage unit to pressure lower than the atmospheric pressure; and a control unit which controls the pressure-reducing mechanism, wherein the control unit lets the pressure-reducing mechanism operate when the liquid leakage detector detects liquid leakage.

10. A method of detecting liquid leakage in which liquid leakage is detected using the liquid leakage detector according to claim 1, the method comprising:

a step of storing an amount of a liquid at the time when liquid leakage is detected in the first liquid detection unit in a case in which liquid leakage is again detected after the liquid leakage detected in the first liquid detection unit is repaired; and a step of determining whether the liquid leakage has occurred in accordance with a calculation result obtained by subtracting the stored amount of the liquid from an amount of a liquid detected in the first liquid detection unit.

* * * * *